United States Patent [19]
Latina

[11] Patent Number: 5,152,760
[45] Date of Patent: Oct. 6, 1992

[54] NON-INVASIVE SCLEROSTOMY

[75] Inventor: Mark A. Latina, North Andover, Mass.

[73] Assignee: The General Hospital Corporation, Boston, Mass.

[21] Appl. No.: 746,209

[22] Filed: Aug. 15, 1991

Related U.S. Application Data

[63] Continuation of Ser. No. 627,883, Dec. 13, 1990, abandoned, which is a continuation of Ser. No. 464,722, Jan. 12, 1990, abandoned, which is a continuation of Ser. No. 325,201, Mar. 17, 1989, abandoned.

[51] Int. Cl.⁵ .............................................. A61B 17/32
[52] U.S. Cl. .......................................... 606/6; 128/395
[58] Field of Search ........................... 128/6, 395–398; 606/3–7

[56] References Cited

U.S. PATENT DOCUMENTS

| | | | |
|---|---|---|---|
| 3,884,236 | 5/1985 | Krasnov | 606/6 |
| 3,982,541 | 9/1976 | L'Esperance | 128/395 |
| 4,164,222 | 8/1979 | Prokhorav et al. | 606/6 |
| 4,525,842 | 6/1985 | Myers | 606/6 |
| 4,558,698 | 12/1985 | O'Dell | 606/6 |
| 4,633,866 | 1/1987 | Peyman et al. | 128/303.1 |
| 4,641,650 | 3/1987 | Mok | 606/7 |
| 4,651,739 | 3/1987 | Oseroff et al. | 128/375 |
| 4,776,335 | 10/1988 | Nakanishi et al. | 128/303.1 |
| 4,782,819 | 11/1988 | Adair | 128/6 |
| 4,846,172 | 7/1989 | Berlin | 128/303.1 |

OTHER PUBLICATIONS

Brown et al., Arch Ophthamol 105:133–136 (Jan. 1987).
Berlin, et al., American Journal of Ophthalmology, 103:713–714, (May, 1987).
Gaasterland et al., Ophthalmic Surgery, 18 (4):254–256, (Apr. 1987).
Higginbotham et al., Ophthalmology, 95 (3):385–390 (1988).
Federman et all, Ophthalmic Surgery, 18 (10):726–727 (Oct. 1987).
Jaffe et al., American Juornal of Ophthalmoloyg, 106:391–396 (Oct. 1988).
Latina et al., Lasers in Surgery and Medicine, 8:233–240.
March et al., Ophthalmic Surgery, 16 (5):328–330 (1985).
March et al., American Journal of Ophthalmology, 104:432–433 (1987).
March et al., Lasers in Surgery and Medicine, 7:353–354 (1987).

*Primary Examiner*—Max Hindenburg
*Attorney, Agent, or Firm*—Fish & Richardson

[57] ABSTRACT

A non-invasive method for treatment of glaucoma by selective ablation of sclera of a living human eye. The method includes providing a slit lamp laser system including a source of pulsed laser light and a gonio lens adapted to withstand pulsed laser light having energy of greater than 100 mJ pulse. The method further includes focusing the laser light on the sclera, and adjusting the light to a spot diameter of between 100 and 300 microns, a pulse width of between 1 and 30 microseconds, a pulse energy of between 75 andn 250 mJ, and a cone angle of between 8 and 15 degrees. The sclera is then repeatedly illuminated with single pulses of laser light until the sclera is perforated.

11 Claims, 1 Drawing Sheet

NON-INVASIVE SCLEROSTOMY

This is a continuation of Ser. No. 07/627,883 filed on Dec. 13, 1990 now abandoned, which is a continuation of Ser. No. 07/464,722 filed on Jan. 12, 1990, now abandoned, which is a continuation of Ser. No. 07/325,201 filed on Mar. 17, 1989, now abandoned.

BACKGROUND OF THE INVENTION

This invention relates to methods for treatment of glaucoma by use of a laser to create a perforation in the sclera.

Glaucoma is a potentially debilitating disease of the eye in which the intraocular pressure of fluid within the eye rises above normal levels. Glaucoma is generally treated by a surgical procedure where a small hole is introduced through the sclera, which is the outer coating of the eye, to allow fluid within the eye to drain into the subconjunctival space, between the conjunctiva and the sclera. Laser light has been used to create such a hole. For example, in 1969 L'Esperance increased absorption of the sclera in the visible region by injection of Indian ink, to allow use of a continuous wave argon ion laser to create a scleral hole. L'Esperance "Laser Trabeculosclerostomy in Ophthalmic Lasers: Photocoagulation, Photoradiation, and Surgery." St. Louis: C. V. Mosby Co., 538–543, 1969. In addition, Latina et al. describe the development of an ab interno laser sclerostomy using a gonio lens technique. Latina et al. ARVO Abstract, p. 254, No. 12, 1986. Methylene blue was applied iontophoretically to the sclera and the sclera then ablated by use of one microsecond long dye-laser pulses at 660 nanometers delivered through a 600 micron optical fiber. Ablation was observed at 50 milliJoules (mJ) per pulse. The authors state that the "potential of this technique for clinical use is being investigated." In 1987, Latina et al., ARVO, No. 11, described ab-interno scleral ablations using one microsecond long pulses at energies of between 30 and 40 mJ per pulse. They state that the method utilizes visible radiation "which offers the potential for developing a minimal invasive or non-invasive filtering procedure, since the laser energy can be delivered via an optical fiber or slit lamp/gonio-lens technique."

SUMMARY OF THE INVENTION

The invention features a non-invasive method for treatment of glaucoma by selective ablation of sclera of a living human eye. The method includes providing a slit lamp laser system including a source of pulsed laser light and a gonio lens adapted to withstand pulsed laser light having energy of greater than 100 mJ per pulse. The method further includes focusing the laser light on the sclera, and adjusting the light to a spot diameter of between 100 and 300 microns, a pulse width of between 1 and 30 microseconds, a pulse energy of between 75 and 250 mJ, and a cone angle of between 8 and 15 degrees. The sclera is then repeatedly illuminated with single pulses of the laser light until the sclera is perforated.

In preferred embodiments, the method further includes the step of dying the sclera with a dye which enhances the optical absorption by the sclera of the laser light; the laser light has a wavelength which is absorbed by the dye, most preferably the dye is water soluble, non-toxic and ionized or charged in solution, e.g., methylene blue, and the wavelength is about 666 nm.

In other preferred embodiments the spot diameter is between 100 and 200 microns; the pulse width is between 5 and 25 microseconds; the pulse energy is between 75 and 200 mJ; the cone angle is between and 10 and 13 degrees; the sclera is illuminated with between 10 and 15 pulses; the dye is applied iontophoretically; and the laser is a flashlamp pulsed-dye laser, or a ruby-pulsed dye laser.

This invention provides a non-invasive method for ablating a small section of sclera with minimal damage to surrounding tissue. The laser light has a set of parameters that minimizes damage to surrounding tissues and prevents potentially harmful acoustical affects of the laser light. Because no incision is required, the number of complications inherent in the surgery are minimized. In addition, the level of fibroblast proliferation, and thence subconjunctival scars is reduced, and permanancy of the ablated area is increased.

Other features and advantages of the invention will be apparent from the following description of the preferred embodiments thereof, and from the claims.

DESCRIPTION OF THE PREFERRED EMBODIMENTS

Figure 1:
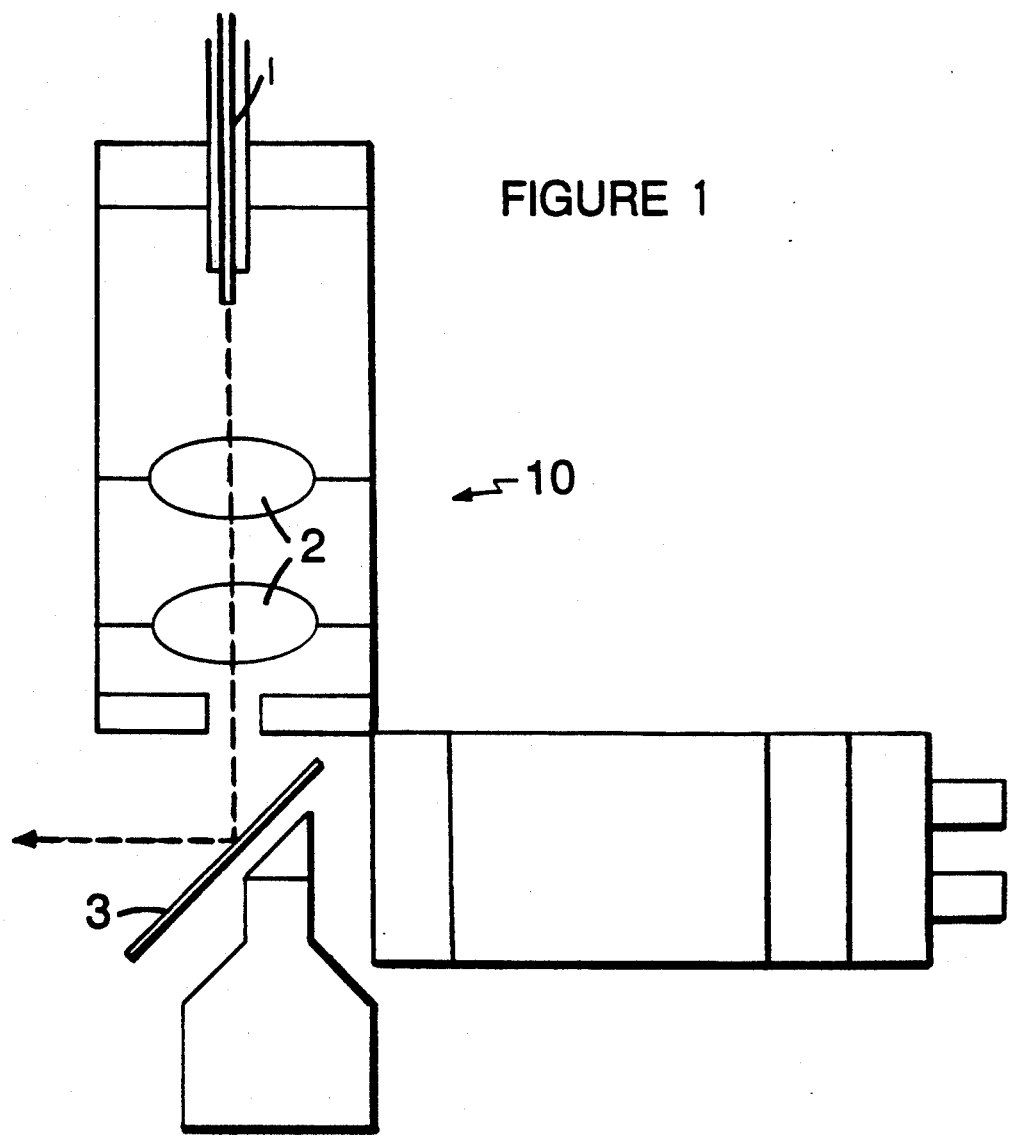

The drawing will first briefly be described.

DRAWING

The Figure is a diagramatic representation of a slit lamp delivery system of the invention.

STRUCTURE

Referring to the Figure, a slit lamp delivery system 10 includes a 600 to 200 micron or 300 to 100 micron tapered optical fiber 1 (FiberGuide) providing a 200 or 100 micron diameter spot at the sample site. In the delivery system the tapered quartz optical fiber is coupled to the output of the laser, and the narrow end held in place at the slit-lamp with a fiberoptic clamp inserted into the delivery device. Two 12 centimeter achromatic focal lenses, 2, of 40 millimeter diameter are provided along with a dichroic mirror, 3, that reflects lights at wavelengths greater than 668 millimeters. The laser source is a modified Candela SPTL-1P flash lamp pumped dye-laser, or modified Candela SPTL flash lamp pulsed dye-laser, using Sulfarhodamine dye (Exciton Corp.).

The goniolens is adapted to withstand the high peak powers of the laser (about 200 mJ), and possesses a mirror angle appropriate for use in the method of this invention. The CGF goniolens of Lasag Corp. possesses these qualities; March et al., 18 Ophthalmic Surgery, 513, 1937. The lens is an aberation free, entirely glass lens. One surface has a 68 degree angle and is coated to provide a reflecting surface. The acrylic scleral flange of the lens helps to restrict tilting of the lens, but maintains elevation of the conjunctiva when suitably positioned.

The parameters suitable for use of the above delivery system are chosen to minimize damage that may occur to surrounding tissue, and to maximize the chance for success of penetration of the desired tissue. Generally, the pulse width of the delivery system is chosen to have at least an 80 percent chance of making a crater in the sclera, but to have a low acoustic effect so that the tissue does not explode when irradiated. Preferably, the pulse width is between 5 and 30 microseconds, a width lower than this having too great an acoustic effect on the tissue in the eye, and a width greater than this having an insufficient chance of producing a crater without significant thermal damage to surrounding tissues.

It is important that the delivery system cause perforation and not just ablation of the sclera. Thus, the pulse energy of the delivery system is chosen to allow perforation of the sclera 80 percent of the time. Again, this energy is chosen to reduce the acoustic effect of the laser light. Generally, the pulse energy is between 75 and 250 mJ.

The spot diameter is chosen such that sufficient energy is provided along the laser light to allow penetration of the sclera and not just ablation. Too small a spot diameter will not allow sufficient energy to be carried along the light, and too large a size requires significantly more energy to penetrate the sclera. A high energy may also have dangerous effects within the eye. Generally, the spot diameter is between 100 and 300 micron.

The cone angle, or numerical aperture, of the delivery system is chosen to ensure that the laser energy will not damage tissues traversed by the laser light prior to reaching the sclera, or deeper tissue within the eye, and concentrates the laser light on the sclera. The angle must not be so low that damage to the cornea results. Generally, the cone angle is between 8 and 15 degrees.

METHOD

There follows an example of use of the above laser for scleral perforation. This example is not limiting to the invention. In this example, laser parameters were chosen to provide a 90% chance of scleral perforation.

Prior to the treatment with the laser, the eye to be treated was anethestized with topical proparicaine. After placement of a lid speculum, the site for the filtration channel was chosen by standard technique. At this site, the sclera was focally dyed at the limbus with iontophoretically applied methylene blue dye (1% solution in distilled water) for a period of 5 minutes or until dye was be visualized within the anterior chamber, at a current of 200 to 400 microamperes. At least a 1 mm diameter dyed spot is required to ensure adequate penetration when irradiated by the laser light. The patient was then seated at the laser slit-lamp and positioned appropriately. In order to insure that the dye had penetrated the entire thickness of sclera, a single mirror qonioscopic lens was placed on the eye to visualize the presence of dye on the internal surface of the sclera, and to insure that the position of the dyed region was correct. The region of the dyed conjunctiva was then ballooned off the sclera with an injection of a viscoelastic agent, such as Healon TM (Pharmacia) or Viscoat TM, (Cooper Vision) using a 27 gauge needle inserted at a site adjacent to the planned filtration bleb.

The above all-glass goniolens with a 68 degree mirror was placed on the eye with methylcellulose and the dyed region of the sclera within the anterior chamber visualized through the slit-lamp. Using the laser aiming light, the laser was focused onto the dyed region. The light was then slightly defocused into the sclera, termed burying the beam, and the laser fired manually in single pulse mode. The ablated sclera was then visualized, and the laser light refocused into the ablation crater and the laser fired manually. This process was continued until a perforation through the sclera was visualized, or there was turbulent flow in the region of the newly created sclerostomy, indicating free flow of aqueous from the anterior chamber into the the subconjunctival space. The gonio-lens was then removed from the eye and the conjunctiva inspected for bleb formation. The intraocular pressure was then measured by applanation tonometry. Subconjunctival steriod was injected at 180 degrees from the bleb site, and topical atropine 1% and polysporin ointment applied to the treated eye. The patient was continued on topical Prednisilone acetate 1% drops 4–6 times a day, and Atropine 1% drops twice a day.

The purpose of the method of this invention is to create a channel through the entire thickness of the sclera. As discussed above, the laser parameters were chosen in the above example to give a 90% chance of reaching this endpoint. These parameters were a pulse width of 1.5 usec; a pulse energy starting at 75 mJ and increasing to 125 mJ; an initial spot diameter of 100 um, increased 50 um to 100 um as the procedure progresses; and firing the laser in single pulse mode.

Other embodiments are within the following claims.

I claim:

1. A non-invasive method for treatment of glaucoma by selective ablation of sclera of a living human eye, comprising the steps of:
   a) providing a slit lamp laser system comprising a source of pulsed laser light and a goniolens adapted to withstand pulsed laser light having energy of greater than 100 mJ per pulse,
   b) focusing said laser on the sclera,
   c) adjusting said laser light to a spot diameter of between 100 and 300 microns, a pulse width of between 1 and 30 microseconds, a pulse energy of between 75 and 250 mJ, and a cone angle of between 8 and 15 degrees, and
   d) repeatedly illuminating the sclera with single pulses of said laser light until the sclera is perforated.

2. The method of claim 1, further comprising the step of dying the sclera with a dye which enhances the optical absorption by the sclera of said laser light.

3. The method of claim 2 wherein said laser light has a wavelength which is absorbed by said dye.

4. The method of claim 3 wherein said sclera is dyed with methylene blue, and said laser light has a wavelength of light about 666 nanometers.

5. The method of the claim 4 wherein said dye is applied iontophoretically.

6. The method of claim 1 wherein said spot diameter is between 100 and 200 microns.

7. The method of claim 1 wherein said pulse width is between 5 and 25 microseconds.

8. The method of claim 1 wherein said pulse energy is between 75 and 200 mJ.

9. The method of claim 1 wherein said cone angle is between about 10 and 13 degrees.

10. The method of claim 1 wherein said sclera is illuminated with between 10 and 15 pulses.

11. The method of claim 1, wherein said laser comprises a flashlamp pulsed-dye laser or ruby-pulsed dye laser.

* * * * *